United States Patent [19]
Cauwet et al.

[11] Patent Number: 5,756,079
[45] Date of Patent: May 26, 1998

[54] COSMETIC COMPOSITIONS CONTAINING AT LEAST ONE ANIONIC SURFACTANT OF ALKYLGALACTOSIDE URONATE TYPE AND AT LEAST ONE NONIONIC SURFACTANT OF ALKYLPOLYGLYCOSIDE AND/OR POLYGLYCEROLATED TYPE

[75] Inventors: Daniele Cauwet, Paris; Claude Dubief, Le Chesnay, both of France

[73] Assignee: L'Oreal, Paris, France

[21] Appl. No.: 556,907

[22] PCT Filed: May 31, 1994

[86] PCT No.: PCT/FR94/00630
§ 371 Date: Nov. 29, 1995
§ 102(e) Date: Nov. 29, 1995

[87] PCT Pub. No.: WO94/27572
PCT Pub. Date: Dec. 8, 1994

[30] Foreign Application Priority Data

Jun. 1, 1993 [FR] France .................... 93 06529

[51] Int. Cl.⁶ .............................. A61K 7/06; A61K 7/00
[52] U.S. Cl. ........................ 424/70.19; 424/70.22; 424/70.31; 424/401
[58] Field of Search .................. 424/70.22, 70.31, 424/401, 70.19

[56] References Cited

FOREIGN PATENT DOCUMENTS

| 0 532 370 | 7/1993 | European Pat. Off. . |
| 0550276 | 7/1993 | European Pat. Off. . |
| 9302092 | 2/1993 | WIPO . |

Primary Examiner—Sally Gardner-Lane
Attorney, Agent, or Firm—Jacobson, Price, Holman & Stern, PLLC

[57] ABSTRACT

Cosmetic compositions containing in an aqueous medium an alkylgalactoside uronate and a non-ionic alkylpolyglycoside and/or polyglycerol type surface-active agents and their use in the treatment or washing of keratinous materials. The alkylgalactoside uronate is based on formula (I):

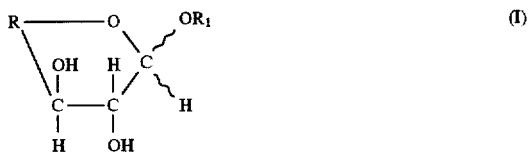

$R_1$ is a $C_8$–$C_{22}$ alkyl;
R is

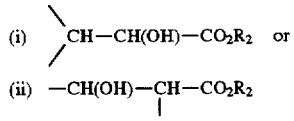

with the carbon carrying the hydroxyl groups being linked to the endocyclic oxygen atom;
$R_2$ is hydrogen, an alkaline metal, an alkaline-earth metal or a quaternary ammonium group.

19 Claims, No Drawings

COSMETIC COMPOSITIONS CONTAINING AT LEAST ONE ANIONIC SURFACTANT OF ALKYLGALACTOSIDE URONATE TYPE AND AT LEAST ONE NONIONIC SURFACTANT OF ALKYLPOLYGLYCOSIDE AND/OR POLYGLYCEROLATED TYPE

This application is filed under 37 C.F.R. 371 and claims a priority date of May 5, 1994 based on PCT/FR94/00630 and a priority date of Jun. 1, 1993 under 35 U.S.C. 119.

The invention relates to cosmetic compositions containing at least one anionic surfactant of alkylgalactoside uronate type and at least one nonionic surfactant of alkylpolyglycoside and/or polyglycerolated type.

Compositions for washing the hair or the skin are generally formulated from anionic or nonionic surfactants or their mixtures, optionally in the presence of amphoteric surfactants.

Hair attacked by atmospheric agents such as light or chemical treatments and washed with conventional washing compositions is difficult to disentangle and this disadvantage is found to be further accentuated in the case of fine hair.

Anionic surfactants of alkylgalactoside uronate type have already been recommended in washing compositions for the hair. They have been described in Patent Application EP 0,532,370.

Nonionic surfactants of the alkylpolyglycoside or polyglycerolated family have also been used in cosmetic washing compositions. These are gentle, well tolerated and biodegradable detergents.

Compositions for washing the hair which use these anionic or nonionic surfactants alone do not lead to good cosmetic properties; in particular, the disentangling of wet hair is difficult and the qualities of the lathers are unsatisfactory.

The Applicant Company has just surprisingly discovered that the combination, in washing and/or treating compositions for keratinous substances, of an anionic surfactant of alkylgalactoside uronate type and of a nonionic surfactant of alkylpolyglycoside and/or polyglycerolated type conferred improved disentangling properties on these compositions.

Moreover, the combination in accordance with the present invention makes it possible to obtain a copious, compact and very gentle lather.

In addition, the. Applicant Company has observed that cosmetic compositions containing such a combination conferred good cosmetic properties, such as softness and a pleasant feel, on keratinous substances.

The subject of the present invention is therefore cosmetic compositions containing at least one anionic surfactant of alkylgalactoside uronate type and at least one nonionic surfactant of alkylpolyglycoside and/or polyglycerolated type.

Another subject of the invention consists of the use of these compositions for treating and/or washing keratinous substances such as the hair or the skin.

Another subject relates to a cosmetic treatment process for the hair or for the skin by means of the compositions of the invention; washing and treatment processes for the hair being preferred.

The cosmetic compositions according to the invention contain, in a cosmetically acceptable aqueous medium:

(A) at least one anionic surfactant of alkylgalactoside uronate type of formula:

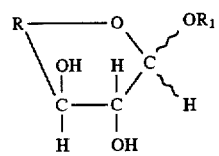

in which:

$R_1$ denotes a linear or branched alkyl radical containing 8 to 22 carbon atoms.

R denotes a group

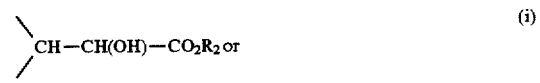

in which the carbon carrying the hydroxyl group is connected to the endocyclic oxygen atom; $R_2$ being hydrogen, an alkali metal, an alkaline-earth metal or a quaternary ammonium group which is unsubstituted or substituted by alkyl or hydroxyalkyl radicals or derived from amino acids.

(B) and at least one nonionic surfactant of alkylpolyglycoside and/or polyglycerolated type.

Anionic surfactants of alkylgalactoside uronate type of formula (I) are known and may be prepared according to the processes described in Patent Application EP-A-0,532,370.

The alkali metal is in particular sodium or potassium and the alkaline-earth metal is preferably magnesium. Mention may be made, as quaternary ammonium salts, of the salts of ammonia, of triethanolamine, of monoethanolamine, of 2-amino-2-methyl-1,3-propanediol or of 2-methyl-2-amino-1-propanol; the amino acid is in particular histidine, arginine or lysine.

Use is preferably made of the compounds of formula (I) in which the $R_1$ radical denotes a $C_8$–$C_{14}$ alkyl and more particularly those having a decyl radical.

Use is in particular made of the following compounds:

Sodium decyl α-D-galactopyranoside uronate:

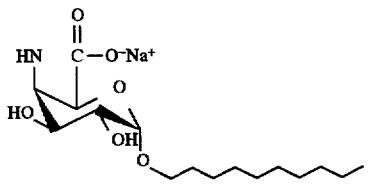

Sodium decyl β-D-galactopyranoside uronate:

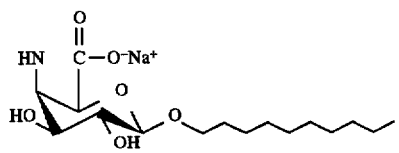

Sodium decyl α-D-galactofuranoside uronate:

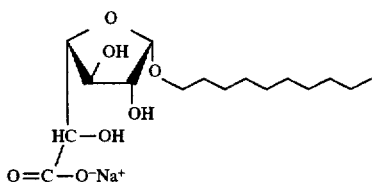

Sodium decyl β-D-galactofuranoside uronate:

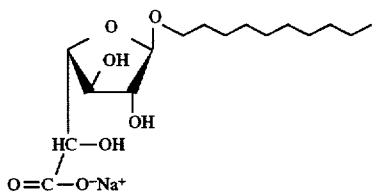

The alkylpolyglycosides which can be used in accordance with the invention correspond in particular to the following formula (II)

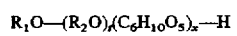

$$R_1O\text{—}(R_2O)_t(C_6H_{10}O_5)_x\text{—}H \qquad (II)$$

corresponding to the expanded structure (III):

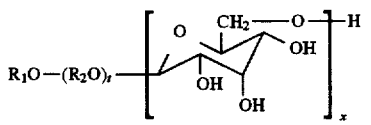

(III)

in which, $R_1$ denotes a $C_8$–$C_{24}$, straight- or branched-chain alkyl or alkenyl radical or a mixture of $C_8$–$C_{24}$, straight- or branched-chain alkyl or alkenyl radicals, $R_2$ is a $C_2$–$C_4$ alkylene radical, t is between 0 and 10 and preferably between 0 and 4, x is a number between 1 and 15.

The preferred compounds are those in which t is equal to 0.

The alkylpolyglycoside compounds of expanded formula (III) defined above, used in accordance with the invention, are preferably represented by the products sold by the Company Henkel under the name APG, such as the products APG 300, APG 350, APG 500, APG 550, APG 625, APG base 10-12; or under the name Plantaren, such as the products Plantaren 300, Plantaren 600, Plantaren 1200 CS/UL or Plantaren 2000 CS/UL; the products sold by the Company Seppic under the names Triton CG 110 (or Oramix CG 110) and Triton CG 312 (or Oramix NS 10); or those sold by the Company BASF under the name Lutensol GD 70.

The nonionic surfactants of the polyglycerolated type used in accordance with the present invention are preferably chosen from the following polyhydroxypropyl ether compounds:

(A) the compounds corresponding to the formula (IV):

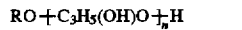

$$RO\text{—}\!\!+\!\!C_3H_5(OH)O\!\!+\!\!_n H \qquad (IV)$$

in which the [$C_3H_5(OH)O$] group represents the following structures; taken together or separately

$$\text{—}CH_2CHOH\text{—}CH_2O\text{—} \qquad (IVa)$$

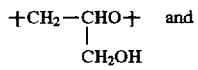

$$\text{—}CH_2\text{—}CHO\text{—} \text{ and} \qquad (IVb)$$
$$\qquad\quad |$$
$$\quad\ CH_2OH$$

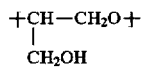

$$\text{—}CH\text{—}CH_2O\text{—} \qquad (IVc)$$
$$|$$
$$CH_2OH$$

and R and n have one of the meanings hereinbelow:

a) R represents a $C_{10}$–$C_{14}$ alkyl radical or a mixture of $C_{10}$–$C_{14}$ alkyl radicals and n is a whole or decimal number from 2 to 10, preferably 3 to 6;

b) R represents a residue:

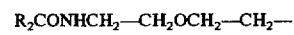

$$R_2CONHCH_2\text{—}CH_2OCH_2\text{—}CH_2\text{—} \qquad (V)$$

where $R_2$ denotes a $C_{11}$–$C_{17}$ alkyl and/or alkenyl radical or a mixture of $C_{11}$–$C_{17}$ alkyl and/or alkenyl radicals and n denotes a whole or decimal number from 1 to 5 and preferably from 1.5 to 4;

c) R represents a residue:

$$R_3\text{—}CHOH\text{—}CH_2\text{—} \qquad (VI)$$

where $R_3$ denotes a $C_7$–$C_{21}$ aliphatic, cycloaliphatic or arylaliphatic radical and their mixtures, the aliphatic chains denoting in particular alkyl chains which can contain from 1 to 6 ether, thioether and/or hydroxymethylene groups, and n denotes a whole or decimal number from 1 to 10.

These surfactants of formula (IV) may be prepared according to the processes described in Patents FR 1,477, 048, 2,328,763 and 2,091,516.

(B) The compounds prepared by condensation, using acid catalysis, of 2 to 10, and preferably of 2.5 to 6, mol of glycidol per mole of alcohol or of alpha-diol containing 10 to 14 carbon atoms, at a temperature of 50° to 120° C., the glycidol being slowly added to the alcohol or to the alpha-diol. The process for the preparation of these compounds is described in Patent FR-A-2,169,787.

(C) The polyhydroxypropyl ether compounds prepared by polyaddition of glycerol monochlorohydrin to a polyhydroxylated organic compound in the presence of a strong base with removal, by distillation, of the water as it is formed. These compounds are described in French Patent FR-A-2,574,786.

Among the nonionic surfactants of the polyhydroxypropyl ether family described in paragraphs (A), (B) and (C) above, the preferred compounds are represented by the formulae:

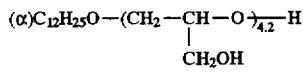

$$(\alpha)C_{12}H_{25}O\text{—}(CH_2\text{—}CH\text{—}O)_{\overline{4.2}}H \qquad (VII)$$
$$\qquad\qquad\qquad\qquad |$$
$$\qquad\qquad\qquad CH_2OH$$

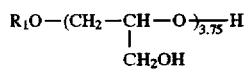

$$R_1O\text{—}(CH_2\text{—}CH\text{—}O)_{\overline{3.75}}H \qquad (VIII)$$
$$\qquad\qquad |$$
$$\qquad CH_2OH$$

where $R_1$ denotes a mixture of $C_{10}H_{21}$ and $C_{12}H_{25}$ alkyl radicals;

(β) the compounds prepared by condensation, using alkaline catalysis, of 3.5 mol of glycidol with an alpha-diol having 12 carbon atoms, according to the process described in Patent FR-A-2,091,516;

(γ) the compounds corresponding to the formula:

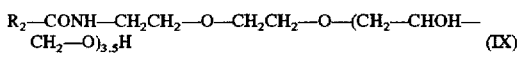

$$R_2-CONH-CH_2CH_2-O-CH_2CH_2-O-(CH_2-CHOH-CH_2-O)_{3.5}H \quad (IX)$$

where $R_2$ denotes a mixture of radicals comprising the following alkyl and alkenyl radicals: $C_{11}H_{23}$, $C_{13}H_{27}$, the radicals derived from coconut fatty acids and the radical derived from oleic acid;

(δ) the compounds prepared by condensation of 3.5 mol of glycidol with a mixture of $C_{11}$–$C_{14}$ alpha-diols, described in Patent FR-A-2,091,516;

(ε) the compounds prepared by condensation of 2.5 mol of glycerol monochlorohydrin with 1,2-dodecanediol in the presence of sodium hydroxide.

The alkylgalactoside uronates of formula (I) are used in the compositions in accordance with the invention in proportions preferably of between 0.5 and 30% by weight with respect to the total weight of the composition.

The nonionic alkylpolyglycoside and/or polyglycerolated surfactants are used in the compositions in accordance with the invention in proportions preferably of between 0.5 and 30% by weight with respect to the total weight of the composition.

If the compositions according to the invention are not used for washing keratinous substances, the total concentration of anionic surfactants of formula (I) and of nonionic alkylpolyglycoside and/or polyglycerolated surfactants is between 1 and 10% and more particularly between 1 and 5% by weight with respect to the total weight of the composition. These compositions are used in particular as compositions to be rinsed, applied before or after shampooing, dyeing, bleaching, perming or hair straightening, or in a composition for dyeing, bleaching, perming or straightening hair.

When the compositions according to the invention are washing compositions, they contain the surfactants of formula (I) and the nonionic alkylpolyglycoside and/or polyglycerolated surfactants in a total concentration of between 5 and 60% by weight and preferably between 8 and 40% by weight with respect to the total weight of the composition.

The compositions can furthermore contain additional surfactants of anionic, nonionic, amphoteric, zwitterionic or cationic nature.

Among the anionic surfactants, there may be mentioned the alkali metal salts, the ammonium salts, the amine salts, the aminoalcohol salts or the magnesium salts of the following compounds: the fatty acids, alkyl sulfates, alkyl ether sulfates, alkylamidoether sulfates, alkylarylpolyether sulfates or monoglyceride sulfates; the alkylsulfonates, alkylethersulfonates, alkylamidesulfonates, alkylarylsulfonates, olefinsulfonates or paraffinsulfonates; the alkylsulfosuccinates, alkylethersulfosuccinates or alkylamidesulfosuccinates; the alkylsulfosuccinamates, alkylsulfoacetates or alkyl ether phosphates; the acylsarcosinates, acylglutamates or N-acyltaurates; or the isethionates.

The alkyl or acyl radical of these various compounds generally consists of a carbon chain containing from 10 to 20 carbon atoms.

It is also possible to use weakly anionic surfactants, such as the polyoxyalkylenated alkyl amide or alkyl ether carboxylic acids, such as those containing 2 to 50 ethylene oxide groups.

The nonionic surfactants are more particularly chosen from the polyethoxylated or polypropoxylated alcohols, α-diols, alkylphenols and fatty acids, with a fatty chain containing 8 to 18 carbon atoms, the number of ethylene oxide or propylene oxide groups being between 2 and 50 and the number of glycerol groups being between 2 and 30.

It is more particularly possible to mention the copolymers of ethylene oxide and of propylene oxide; the condensates of ethylene oxide and of propylene oxide with fatty alcohols; the polyethoxylated fatty amides having preferably 2 to 30 mol of ethylene oxide; the polyethoxylated fatty amines having preferably 2 to 30 mol of ethylene oxide; the oxyethylenated fatty acid esters of sorbitan having preferably 2 to 30 mol of ethylene oxide; the fatty acid esters of sugar, the fatty acid esters of polyethylene glycol, the fatty acid esters of glycols; or the amine oxides such as the oxides of $(C_{10}$–$C_{14})$alkylamines or of N-acylamidopropylmorpholine.

The preferred amphoteric or zwitterionic surfactants are the derivatives of secondary or tertiary aliphatic amines, in which the aliphatic radical is a linear or branched chain containing 8 to 18 carbon atoms and which contains at least one water-solubilizing carboxylate, sulfonate, sulfate, phosphate or phosphonate anionic group; the $(C_8$–$C_{20})$ alkylbetaines, the sulfobetaines, the $(C_8$–$C_{20})$alkylamido $(C_1$–$C_6)$alkylbetaines or the $(C_8$–$C_{20})$alkylamido$(C_1$–$C_6)$ alkylsulfobetaines.

It is also possible to mention the alkylpeptides or the alkylimidazolium betaines.

Among the amine derivatives, there may be mentioned the products marketed under the name "Miranol", such as those described in U.S. Pat. Nos. 2,528,378 and 2,781,354 or listed in the CTFA dictionary, 3rd edition, 1982, under the names of Amphocarboxyglycinates or of Amphocarboxypropionates.

The cationic surfactants are chosen from the quaternary ammonium salts, such as the $(C_8$–$C_{22})$ alkyltrimethylammonium halides, the $(C_8$–$C_{22})$ dialkyldimethylammonium halides or the $(C_8$–$C_{22})$ alkyldimethylhydroxyethylammonium halides.

The additional cosurfactants can represent up to 50% of the total weight of the surfactants present in the composition.

The pH of the compositions in accordance with the invention is generally between 2 and 10.5 and more particularly between 3 and 8.

Insofar as the cosmetically acceptable medium of the composition according to the invention is an aqueous medium, it may consist solely of water or of a mixture of water and of a cosmetically acceptable solvent, such as $C_1$–$C_4$ lower alcohols, such as ethanol, isopropanol or n-butanol; alkylene glycols, such as propylene glycol; or glycol ethers.

The compositions according to the invention can be provided in the form of a more or less thickened liquid, a gel, an emulsion (milk or cream), an aqueous/alcoholic lotion, a dispersion, a solid bar or an aerosol foam.

The compositions are, for example, emollient lotions, milks or creams, lotions, milks or creams for caring for keratinous substances, make-up removal creams or milks, foundation bases, antisun lotions, milks or creams, lotions, milks or creams for artificial tanning, shaving creams or foams, aftershave lotions, face masks, make-up products for the eyes, nail varnishes, colors and foundations for the face, shampoos, bath or shower products, compositions to be rinsed or not to be rinsed, to be applied before or after shampooing, dyeing, bleaching, perming or hair straightening, or compositions for dyeing, bleaching, perming or straightening the hair.

The compositions in accordance with the invention can also contain, in addition, various additives such as thickening agents, such as polyacrylic acids, cellulose derivatives or esters of fatty acids and of polyethylene glycol; sequestering agents; foam reinforcers; preservatives; fragrances; electrolytes; fatty substances, such as fatty alcohols, ceramides or mineral, vegetable, animal or synthetic oils or waxes; UW screening agents; agents for combating free radicals; pearlescence agents; biocides; antibacterials; antidandruff agents; anti-seborrheic agents; antiparasitic agents; repellents; dyes; pigments; oxidizing agents; reducing agents; moisturizers; anionic, cationic, nonionic or amphoteric polymers, vitamins or α-hydroxy acids.

Treatment of the keratinous substances is carried out by application to these substances of a cosmetically acceptable amount of a composition as defined above.

The process for washing and/or for conditioning the keratinous substances and in particular the hair or the skin in accordance with the invention consists in applying at least one composition as defined above to these substances, this application optionally being followed by a stage of rinsing with water.

The washing compositions can be used as a shampoo but also as a shower gel for washing the hair and the skin, in which case they are applied to the wet skin and hair, which are rinsed after application.

When the compositions are used for conditioning the hair, they are applied to the wet hair, after which it may either be dried or, after an exposure time of 1 to 10 minutes, rinsed with water. It is observed that the wet hair disentangles readily.

The examples which follow are intended to illustrate the invention without having any limiting nature whatsoever.

EXAMPLE 1

Conditioner

| | |
|---|---|
| Sodium decyl D-galactoside uronate | 2 g AM |
| Dodecanediol polyglycerolated with 3.5 mol of glycerol | 1 g AM |
| Mixture of cetylstearyl and oxyethylenated (33 EO) cetylstearyl alcohols, 80/20, sold under the name Dehsconet 390 by Tensia | 5 g |
| Distearyldimethylammonium chloride | 3 g |
| Dyes, fragrance, preservative | |
| water q.s. for | 100 g |
| pH adjusted to 5 with HCl | |

The composition exists in the form of a fluid white cream.

EXAMPLE 2

Foam Bath

| | |
|---|---|
| Sodium decyl D-galactoside uronate | 25 g AM |
| (1,4)-($C_9/C_{10}/C_{11}$ 20/40/40)Alkylpolyglucoside as a 50% aqueous solution, sold under the name of APG 300 by the Company Henkel | 5 g AM |
| Ethers of hexadecanediol (3 mol) and of polyethylene glycol 60 EO | 5 g |
| Dyes, fragrance, preservative | |
| water q.s. for | 100 g |
| pH adjusted to 6 with HCl. | |

The composition has a clear and viscous appearance.

EXAMPLE 3

Shower Gel

| | |
|---|---|
| Sodium decyl D-galactoside uronate | 15 g AM |
| Dodecanediol polyglycerolated with 3.5 mol of glycerol | 10 g AM |
| Pure glycerol | 2 g |
| Oxyethylenated (60 EO) tallow ether of myristil [sic] glycol sold under the name of Elfacos GT 282 S by the Company Akzo | 3 g |
| Dyes, fragrance, preservative | |
| water q.s. for | 100 g |
| pH adjusted to 7.5 with NaOH. | |

The composition has a clear and viscous appearance.

EXAMPLE 4

Shampoo

| | |
|---|---|
| Sodium decyl D-galactoside uronate | 7.5 g AM |
| (1,4)-($C_9/C_{10}/C_{11}$ 20/40/40)Alkylpolyglucoside as a 50% aqueous solution, sold under the name of APG 300 by the Company Henkel | 7.5 g AM |
| Diurethane of oxyethylenated and oxypropylenated alcohols ($C_{16}/C_{18}$) sold under the name of Dapral T 212 by the Company Akzo | 3 g |
| Dyes, fragrance, preservative | |
| water q.s. for | 100 g |
| pH adjusted to 6.4 with HCl. | |

The composition has a clear and viscous appearance.

We claim:

1. Cosmetic composition, comprising, in a cosmetically acceptable aqueous medium:

(A) at least one alkylgalactoside uronate anionic surfactant of formula:

$$
\begin{array}{c}
R-O \diagdown_C{-}OR_1 \\
\diagdown OH \quad H \diagup \\
\mid \quad \mid \diagup \diagdown H \\
C-C \\
\mid \quad \mid \\
H \quad OH
\end{array} \quad (I)
$$

in which $R_1$ denotes a linear or branched alkyl radical containing 8 to 22 carbon atoms, R denotes a group (i) $\diagdown CH-CH(OH)-CO_2R_2$ or
   $\diagup$ (ii) $-CH(OH)-CH-CO_2R_2$,
                $\mid$ in which the carbon carrying the hydroxyl group is connected to the endocyclic oxygen atom; $R_2$ being a hydrogen, an alkali metal, an alkaline-earth metal or a quaternary ammonium group which is unsubstituted or substituted by alkyl or hydroxyalkyl radicals or an amino acid radical, and (B) at least one nonionic surfactant which is an alkylpolyglycoside corresponding to the following formula (II)

 (II)

in which

R$_1$ denotes a C$_8$–C$_{24}$ straight or branched chain alkyl or alkenyl radical or a mixture of C$_8$–C$_{24}$ straight or branched chain alkyl or alkenyl radicals.

R$_2$ is a C$_2$–C$_4$ alkylene radical t is a number between 1 and 10 x is a number between 1 and 15 and/or one or more of the following polyhydroxypropyl ethers A) compounds corresponding to the following formula (IV)

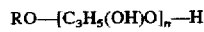

in which each [C$_3$H$_5$(OH)O] group independently represents one of the following structures

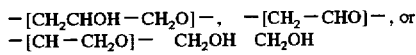

and R and n have one of the meanings herein below:
a) R represents a C$_{10}$–C$_{14}$ alkyl radical or a mixture of C$_{10}$–C$_{14}$ alky radicals and n is a whole number or decimal number from 1 to 10;
b) R represents a residue

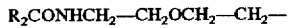

where R$_2$ denotes a C$_{11}$–C$_{17}$ alkyl and/or alkenyl radical or a mixture of C$_{11}$–C$_{17}$ alkyl and/or alkenyl radicals and n denotes a whole or decimal number from 1 to 5;
c) R represents a residue

where R$_3$ denotes a C$_7$–C$_{21}$ aliphatic, cycloaliphatic or arylaliphatic radical and of mixtures thereof and n denotes a whole or decimal number from 1 to 10;

B) compounds prepared by condensation, using acid catalysis of 2 to 10 mol of glycidol per mole of alcohol or of alpha-diol containing 10–14 carbon atoms, at a temperature of 50° to 120° C., the glycidol being added to the alcohol or to the alpha-diol; or C) compounds prepared by polyaddition of glycerol monochlorohydrin to a polyhydroxylated organic compound in the presence of a base with removal, by distillation of the water as it is formed; wherein said alkylgalactoside uronate anionic surfactant is present at a concentration of 0.5–30% by weight of the total composition and said nonionic surfactant is present in a concentration of 0.5–30% by weight of the total composition.

2. Composition according to claim 1, wherein, in the formula (I), the radical R$_2$ denotes sodium or potassium; magnesium; or the quaternary ammonium group derived from ammonia, triethanolamine, monoethanolamine, 2-amino-2-methyl-1,3-propanediol, 2-methyl-2-amino-1-propanol, histidine, arginine or lysine.

3. Composition according to claim 1, wherein R$_1$ denotes a C$_8$–C$_{14}$ alkyl.

4. Composition according to claim 1, wherein R$_1$ denotes a decyl radical.

5. Composition according to claim 4, wherein the compound of formula (I) is:

sodium decyl α-D-galactopyranoside uronate,
sodium decyl β-D-galactopyranoside uronate,
sodium decyl α-D-galactofuranoside uronate, or
sodium decyl β-D-galactofuranoside uronate.

6. Composition according to claim 1, wherein the nonionic polyglycerolated surfactants are chosen from the following polyhydroxypropyl ethers:

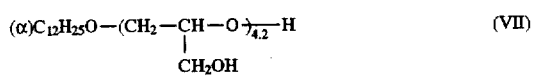 (VII)

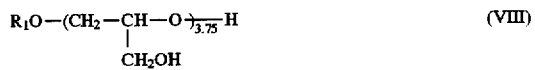 (VIII)

where

R$_1$ denotes a mixture of C$_{10}$H$_{21}$ and C$_{12}$H$_{25}$ alkyl radicals;

(β) the compounds prepared by condensation, using alkaline catalysis, of 3.5 mol of glycidol with an alpha-diol having 12 carbon atoms;

(γ) the compounds corresponding to the formula:

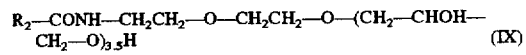 (IX)

where R$_2$ denotes a mixture of radicals comprising the following alkyl and alkenyl radicals: C$_{11}$H$_{23}$, C$_{13}$H$_{27}$, the radicals derived from coconut fatty acids or the radical derived from oleic acid;

(δ) the compounds prepared by condensation of 3.5 mol of glycidol with a mixture of C$_{11}$–C$_{14}$ alpha-diols;

(ε) the compounds prepared by condensation of 2.5 mol of glycerol monochlorohydrin with 1,2-dodecanediol.

7. Composition for conditioning keratinous substances according to claim 1, wherein the total concentration of anionic surfactants of formula (I) and of nonionic alkylpolyglycoside and/or polyglycerolated surfactants is between 1 and 10% by weight with respect to the total weight of the composition.

8. Composition for washing keratinous substances according to claim 1, wherein the total concentration of anionic surfactants of formula (I) and of nonionic alkylpolyglycoside and/or polyglycerolated surfactants is between 5 and 60% by weight with respect to the total weight of the composition.

9. Composition according to claim 1, wherein the composition further contains an additional cosurfactant of anionic, nonionic, amphoteric or cationic type in a proportion ranging up to 50% of the total weight of surfactants.

10. Composition according to claim 9, wherein the additional anionic cosurfactant is chosen from the alkali metal salts, the ammonium salts, the aminoalcohol salts or the magnesium salts of the following compounds: fatty acids, alkyl sulfates, alkyl ether sulfates, alkylamidoether sulfates, alkylarylpolyether sulfates or monoglyceride sulfates; the alkylsulfonates, alkylethersulfonates, alkylamidesulfonates, alkylarylsulfonates, olefinsulfonates or paraffinsulfonates; the alkylsulfosuccinates, alkylethersulfosuccinates or alkylamidesulfosuccinates; the alkylsulfosuccinamates; the alkylsulfoacetates; the alkyl ether phosphates; the acylsarcosinates, acylglutamates or N-acyltaurates; or the isethionates; the alkyl or acyl radical consisting of a carbon chain containing 10 or 20 carbon atoms or polyoxyalkylenated alkyl amide or alkyl ether carboxylic acids.

11. Composition according to claim 9, wherein the additional nonionic cosurfactant is chosen from the polyethoxylated or polypropoxylated alcohols, α-diols, alkylphenols and fatty acids, with a fatty chain containing 8 to 18 carbon atoms, the number of ethylene oxide or propylene oxide groups being between 2 and 50 and the number of glycerol groups being between 2 and 30, the copolymers of ethylene oxide and of propylene oxide; the condensates of ethylene oxide and of propylene oxide with fatty alcohols, the polyethoxylated fatty amides; the polyethoxylated fatty amines; the oxyethylenated fatty acid esters of sorbitan, the fatty acid esters of sugar; the fatty acid esters of polyethylene glycols; the fatty acid esters of glycols; or the amine oxides.

12. Composition according to claim 9, wherein the additional amphoteric cosurfactant is chosen from the derivatives of secondary or tertiary aliphatic amines, in which the aliphatic radical is a linear or branched chain containing 8 to 18 carbon atoms and which contains at least one water-solubilizing carboxylate, sulfonate, sulfate, phosphate or phosphonate anionic group; the $(C_8-C_{20})$alkylbetaines, the sulfobetaines, the $(C_8-C_{20})$alkylamido $(C_1-C_6)$ alkylbetaines or the $(C_8-C_{20})$alkylamido$(C_1-C_6)$ alkylsulfobetaines; the alkylpeptides; or the alkylimidazolium betaines.

13. Composition according to claim 10, wherein the cationic cosurfactant is a quaternary ammonium salt.

14. Composition according to claim 1, wherein the cosmetically acceptable medium consists of water or a mixture of water and of a cosmetically acceptable solvent.

15. Composition according to claim 1, wherein the composition is in the form of a thickened liquid, a gel, an emulsion, an aqueous/alcoholic lotion, a dispersion, a solid bar or an aerosol foam.

16. Composition according to claim 1, wherein the composition further contains additives chosen from foam reinforcers, thickeners, sequestering agents, electrolytes, fragrances, preservatives, fatty alcohols, mineral, vegetable, animal or synthetic oils or waxes, ceramides, UV screening agents, agents for combating free radicals, pearlescence agents, biocides, antibacterials, antidandruff agents, antiseborrheic agents, antiparasitic agents, repellents, dyes, pigments, oxidizing agents, reducing agents, moisturizers, anionic, cationic or nonionic amphoteric polymers, vitamins or α-hydroxy acids.

17. Process for cosmetic washing and/or conditioning of the hair or of the skin, comprising applying an effective amount for washing and/or conditioning the hair or the skin of composition according to claim 1 to the skin or the hair, this application optionally being followed by a rinsing with water.

18. Composition according to claim 1, wherein the polyhydroxypropyl ether is selected from the group consisting of compounds where in formula (IV) R and n is defined in a) and n is 3 to 6, compounds where in formula (IV) R and n is defined in b) and n is 1.5 to 4, compounds prepared by condensation as defined in B) where there are used 2.5 to 6 mol of glycidol and mixtures thereof in a) n is 3 to 6; in b) n is 1.5 to 4; and in (B) there are used 2.5 to 6 mol of glycidol.

19. Composition according to claim 1, wherein t is a number between 0 and 4.

* * * * *